United States Patent [19]

Kalarickal

[11] Patent Number: 4,641,661
[45] Date of Patent: Feb. 10, 1987

[54] ELECTRONIC ALGESIMETER

[76] Inventor: Mathew S. Kalarickal, Kalarickal-Kottayam, Kerala, India, 686018

[21] Appl. No.: 761,790

[22] Filed: Aug. 2, 1985

[51] Int. Cl.⁴ ............................................... A61B 19/00
[52] U.S. Cl. .................. 128/744; 73/862.53; 73/862.67
[58] Field of Search .............................. 128/744, 675; 73/862.53, 862.67, 379

[56] References Cited

U.S. PATENT DOCUMENTS

| | | | |
|---|---|---|---|
| Re. 29,765 | 9/1978 | Crane et al. | 73/862.67 |
| 1,637,421 | 8/1927 | Lipschultz | 128/744 |
| 2,422,520 | 6/1947 | Bartley | 128/744 |
| 2,453,841 | 11/1948 | Gluzek | 128/744 |
| 2,648,328 | 8/1953 | Hathaway et al. | 128/675 |
| 2,678,692 | 5/1954 | Ranseen | 128/744 |
| 2,704,539 | 3/1955 | Fisher | 128/744 |
| 3,074,395 | 1/1963 | Kevorkian | 128/744 |
| 3,088,323 | 5/1963 | Welkowitz et al. | 128/675 |
| 3,189,023 | 6/1965 | Salz et al. | 128/675 |
| 3,240,207 | 3/1966 | Barker et al. | 128/675 |
| 3,662,744 | 5/1972 | Low et al. | 128/744 |
| 3,696,667 | 10/1972 | Foster et al. | 73/862.53 |
| 4,111,052 | 9/1978 | Sniderman | 73/862.67 |
| 4,313,446 | 2/1982 | Kanatani | 128/744 |
| 4,499,903 | 2/1985 | Furst et al. | 128/675 |
| 4,501,148 | 2/1985 | Nicholas et al. | 73/862.67 |

FOREIGN PATENT DOCUMENTS 2704520  8/1978  Fed. Rep. of Germany ... 73/862.53

*Primary Examiner*—Kyle L. Howell
*Assistant Examiner*—David Shay
*Attorney, Agent, or Firm*—Michael Ebert

[57] ABSTRACT

An electronic algesimeter adapted to determine by cutaneous sensation the threshold of pain experienced by a patient at any skin site on the body. The instrument includes a hand-held, pressure-sensitive transducer having projecting therefrom a sensor constituted by a pointed probe. When the point of the probe is pressed against the skin, the transducer then yields an electrical signal proportional to the applied pressure, this signal being fed to a resettable digital display. And when the pressure applied to the skin reaches a threshold value at which the patient experiences pain, a switch is actuated by the patient or the examiner to retain the digital indication at that value whereby it may be read by the examining physician and recorded after the instrument is withdrawn from the skin.

17 Claims, 4 Drawing Figures

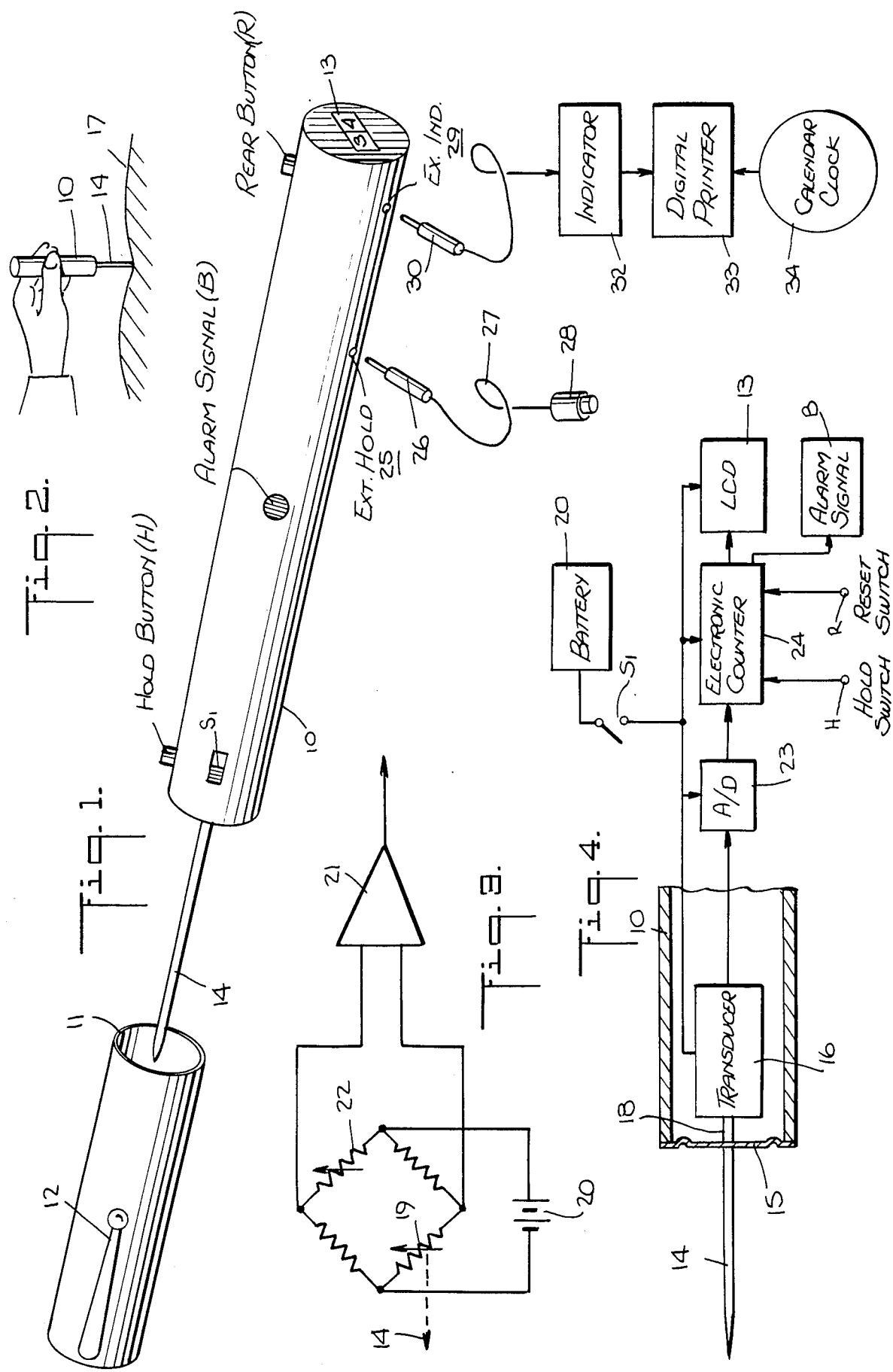

ELECTRONIC ALGESIMETER

BACKGROUND OF INVENTION

1. Field of Invention:

This invention relates generally to medical instruments for testing by means of cutaneous sensation a patient's threshold of pain, and more particularly to an electronic algesimeter which includes a pointed probe that is pressable against the skin of the patient at any desired site, the algesimeter accurately indicating and holding the value of pressure imposed on the skin at the pain threshold to provide a threshold reading whereby by testing the patient from time to time and recording the readings, a diagnostician can from this history determine the changing condition of the patient.

2. Status of the Art

The skin consists of two superposed layers, the epidermis and the dermis. Associated with the skin are receptor organs of touch, temperature, pain and other cutaneous sensations. These receptors include Meissner's corpuscle and Merkel's disc which when stimulated elicit the sensation of touch. The Pacinian corpuscle responds to deep pressure, while stimulation of free nerve endings gives rise to the sensation of pain.

Cutaneous sensations are transmitted from the skin to various regions in the cerebral cortex. Thus, sensations of touch as well as those of warmth and coolness are perceived and interpreted in particular regions of the somesthetic or bodily sensory area of the parietal lobe. The sensation of pain for each side of the body is conducted to the brain independently. Hence, the sensitivity of a particular area of the body may be compared with a reference area on the opposite side thereof. This comparison is useful in diagnosis, for the involvement of the sensory nervous system is unilateral.

Certain neurological and other medical examinations and procedures entail the location and delineation of areas of analgesia or hyposthesia, the former being the absence of pain or touch sensitivity; the latter, reduced pain or touch sensitivity. Also of interest is hyperalgesia, that is, enhanced sensitivity to painful stimuli. Such tests are normally carried out in special examinations for the treatment of neurological disorders as well as in general medical check-ups and in diagnosing various diseases.

Soma-sensory dysfunction due to lesions in the sensory nerves or tracks is at least as common as motor disturbances in clinical neurology. When an injury or disease adversely affects a peripheral nerve, per se, or at different levels of its course to the brain, it is manifested as motor or sensory defects, or as a combination thereof. When there is an involvement of the sensory system, it may affect all sensory modalities or the impairment may be restricted to a particular form of sensation. Two patterns of preferential sensory loss have been recognized. In one, selective loss of pain and temperature develops, while in the other, there is a loss of touch and pressure sensitivity. A third pattern is the simultaneous involvement of all modalities of sensations.

Conventional skin sensitivity test procedures, though useful in screening examinations, are neither quantitative nor selective. The usual clinical procedure to test the sensory function employs a sharpened pin to prick the skin area, the patient reporting to the examiner whether or not he can feel the stimulus and, if he can, the intensity. The examining physician will then ask the patient to compare sensations experienced in the same region on two sides of the body. Abnormality is recognized by the difference in the elicited stimuli. This method is altogether unsatisfactory, save when the defect is very gross, for mild to moderate defects, though significant, are generally missed.

The main drawback incident to the conventional test procedure is that the physical characteristics of the stimuli are essentially undefined variables and the thresholds are not specific, nor are they quantified or validated. The results of such tests are therefore quite indefinite and are not reproducible. The physician is forced to rely on the patient's memory and ability to compare the previous stimuli to the present one. Thus neither the patient nor the doctor can determine whether the applied pin prick stimuli are equal in quantitative rather than in subjective terms. The physician himself can be mistaken because his pin prick stimuli may vary in intensity from site to site and from time to time.

These deficiencies become more pronounced when between each testing there is a substantial gap of a few hours, or of several days or months. In such cases, the physician must depend entirely on the patient's ability to comprehend and remember the differences from previous test occasions. Moreover, the physician himself is not sure whether the pin prick stimuli given on these occasions were of identical magnitude. And if the patient has to be examined at various times by different doctors, the test results become even more unpredictable, for there is no standardization of the applied sensory stimuli.

The need to keep a record of the stimuli required to produce a painful sensation is vital in cases involving nerve injury, surgical repair of the nerves, tropical diseases such as leprosy, and common stroke. In these cases, the recovery usually takes a protracted course with surgical or medical treatment. Hence a periodic review of the sensory function of the affected area is an invaluable guide in arriving at a correct prognosis, and it assists the doctor in deciding whether to interfere medically or surgically at any particular stage during the course of the disease.

As pointed out in the Kerokian U.S. Pat. No. 3,074,795, with a conventional sensitivity test procedure, the muscular coordination required of the medical examiner to make pin pricks with the proper degree of uniformity is exceedingly difficult to attain, particular in older practitioners. In many situations, therefore, the difference in the pain sensitivity reported by the patient may arise, not because of his medical condition, but by reason of variations in the intensity of the pin strikes made by the medical examiner. Thus, in some instances, variations in pain felt by the patient may not indicate the actual pain sensitivity of the skin but may simply be due to the uncertain muscular coordination of the examiner. The factors outlined above render the testing of pain sensation by conventional techniques unreliable, and the results thereof statistically inaccurate.

In order to provide a highly compact skin sensitivity detector, the patent to Fisher, U.S. Pat. No. 2,704,539, discloses a pen-like instrument having a needle secured to one end of a compressible spring disposed within a tubular casing, the needle going through a bore in the front end of the casing. The other end of the spring is attached to a plunger within whose axial bore is a rotatable shaft having a spiral groove, an indicator pin carried by the plunger extending into this groove. The Fisher arrangement is such that when the needle is pressed against the skin of a patient at a selected site, this acts to axially shift the plunger and thereby rotate the shaft and to cause the indicator pin to advance along a pressure-indicating scale.

The advantage of the Fisher arrangement is that it indicates the magnitude of the applied pressure at the threshold of pain. However, the Fisher device has many practical drawbacks. Thus, in order to obtain a threshold reading, the patient must tell the examiner when he experiences pain at the instant it is felt. The examiner must then look at the instrument to read the indicated pressure. Inevitably, there will be a time delay in the reaction time of the doctor to the patient's verbal response to the sensation of pain.

And since the threshold indication on the Fisher device reflects the prevailing degree of pressure exerted on the skin of the patient by the doctor holding the instrument, the doctor may find it difficult to exactly maintain this pressure in the period when he is taking a reading. Consequently, in the time elapsing between the patient's verbal response to pain and the moment the doctor takes a reading, the exerted pressure may change and an inexact reading may be obtained. Further, since in Fisher the needle passes through a bore and encounters friction as it is axially shifted by pressure, this, too, impairs the accuracy of the pressure reading. Another disadvantage of Fisher's meter is that it is non-linear, for the helical spring therein does not have a linear characteristic.

Also of general background interest are the patents to Kanatani, U.S. Pat. No. 4,313,446; Karatsu, U.S. Pat. No. 1,259,820 and Gluzek, U.S. Pat. No. 2,453,841.

SUMMARY OF INVENTION

In view of the foregoing, the main object of this invention is to provide an electronic algesimeter which gives an accurate indication of the value of pressure applied at the threshold of pain and which holds this indication until the indicator is reset by the examiner.

A significant feature of an instrument in accordance with the invention is that it is simple to operate and provides a quantified and calibrated painful stimulus on the patient's skin which is reproducible. The instrument, which includes a pointed probe, is used by the examiner by continuously increasing the pressure applied by the point of the probe on the skin until the patient feels the stimulus, at which critical point the pressure indication is then held. The muscular coordination of the examiner does not come into play in the operation of the instrument for the examiner is given a continuous readout in real time of the pressure he is applying.

More particularly, an object of this invention is to provide an inexpensive electronic algesimeter of the above type that is highly compact so that it may be carried in the breast pocket of the doctor or in his medical bag. The instrument lends itself to use not only at the patient's bedside in a hospital but in emergency rooms, in ambulances and wherever there is an immediate need to conduct a skin sensitivity test, for the instrument in its preferred form is self-sufficient; it requires no external accessories and may be put to immediate use.

Also an object of the invention is to provide an electronic algesimeter which includes an audible or visible warning signal that is activated when the pressure applied to the patient exceeds a safe level, so that no injury will be inflicted on a patient suffering from a gross loss of sensitivity.

Yet another object of the invention is to provide an algesimeter having a digital display on the instrument itself or on a digital display unit external thereto, the external unit being provided with a printer to provide a permanent record of the readings and time and date indications so that a medical history may be developed of a patient's changing conditions.

Still another object of the invention is to provide an algesimeter in which the digital indication of pressure at the instant the patient experiences a sensation of pain is held by means of an external hold switch operated by the patient, a reset button operated by the examiner acting to reset the display for testing of the next skin site, thereby obviating any time delay between the sensation of pain and the held threshold pressure indication. When the patient presses the external hold switch to indicate that he has felt the pain stimulus, the alarm signal will then be activated and the examiner, in response to this signal, will stop the test.

A further object of this invention is to provide in an electronic algesimeter of the above-type an external hold switch operated by the patient and coupled to the algesimeter either by a cable or by a wireless link of the hand-held type, all of which accessories may be carried in the pocket of the physician or in his medical bag.

A still further object of the invention is to provide a hand-held electronic algesimeter with external accessories to be used under hospital or office conditions for recording the test results and for research purposes, the external accessories including a digital display unit which functions in parallel and concurrently with the local digital display on the algesimeter, the external digital display unit being associated with a printer unit which is activated manually or automatically at the end of each test procedure, which accessories are coupled to the algesimeter by a wired or wireless link.

Briefly stated, these objects are attained in an electronic algesimeter adapted to determine by cutaneous sensation the threshold of pain experienced by a patient at any skin site on the body. The instrument includes a hand-held, pressure-sensitive transducer having projecting therefrom a sensor constituted by a pointed probe. When the point of the probe is pressed against the skin, the transducer then yields an electrical signal proportional to the applied pressure, this signal being fed to a resettable digital display. And when the pressure applied to the skin reaches a threshold value at which the patient experiences pain, a switch is actuated by the patient or the examiner to retain the digital indication at that value whereby it may be read by the examining physician and recorded by an external printer unit after the instrument is withdrawn from the skin.

OUTLINE OF DRAWINGS

For a better understanding of the invention as well as other objects and further features thereof, reference is made to the following detailed description to be read in conjunction with the accompanying drawings, wherein:

FIG. 1 is a perspective view of a self-sufficient electronic algesimeter in accordance with the invention;

FIG. 2 illustrates the manner in which the instrument is used;

FIG. 3 shows the transducer circuit; and

FIG. 4 is a schematic diagram of the instrument components.

DESCRIPTION OF INVENTION

Structure of Instrument

Referring now to FIG. 1, there is shown a preferred embodiment of a compact electronic algesimeter in accordance with the invention, the instrument being in a pen-like format. The instrument includes a tubular casing 10, preferably fabricated of synthetic plastic material and a removable cap 11 therefor of the same material having a clip 12 thereon, whereby the instrument may be carried in the manner of a writing pen in the breast pocket of the examining physician.

Mounted on the rear end of the casing is a digital display 13, preferably of the liquid crystal or LCD type having at least two numeric stations so that the numbers 00 to 99 may be displayed. In practice the display may be of the LED type and mounted at any readable position on the casing. Projecting axially from the front end of the case is a pointed sensor probe 14. The probe is in the form of a needle, preferably of stainless steel of standard diameter and length whose point has a predetermined wedge angle appropriate to a skin sensitivity test.

Also mounted on the casing is an on-off switch $S_1$ which is interposed between the battery for supplying power to the instrument and the electronic stages of the instrument. A pilot light or a buzzer B mounted on the casing functions to provide an alarm signal when the pressure applied to the patient exceeds a safe level. A hold button switch H mounted on the casing, when actuated, serves to hold the reading on the display and a reset button switch R also mounted on the casing, serves when actuated to reset the display to zero.

As shown in FIG. 4, needle 14 is mounted at the center of a diaphragm 15 which is coupled to a transducer 16 housed within the casing, the transducer yielding a signal proportional to the pressure exerted thereon by the needle when it is pressed against the skin 17 of a patient at a selected site, as shown in FIG. 2.

The transducer may be of any commercially-available type, such as a potentiometric, a reluctive or a strain gauge transducer. In a potentiometric pressure transducer, a pushrod 18, which in the present arrangement would be coupled to the diaphragm, transfers its displacement to a lever-type wiper arm that slides along a resistance element so that the resistance of the device varies linearly as a function of the applied pressure.

When the potentiometric transducer represented by variable resistance 19 in FIG. 4 is included as an arm in a Wheatstone bridge having a dc voltage from a battery 20 applied to its input diagonals, then the magnitude and polarity of the voltage yielded at the output diagonals will depend on the resistance of the pressure transducer, as determined by the pressure applied to the skin of the patient. This voltage is applied to an amplifier 21 which yields the transducer signal.

By the use of an adjustable balancing resistor 22 in the opposing arm of the bridge, the bridge may be nulled, so that at zero pressure, the output is zero. As pressure is applied and increased, the output voltage of the bridge rises in magnitude in proportion to the applied pressure. Hence the output signal from the transducer is an analog voltage proportional to the pressure exerted on the skin of the patient. In practice, a feedback system may be provided between the output of amplifier 21 and the resistor 22 as to maintain a null condition in the absence of applied pressure regardless of changes in battery voltage or other electrical variables such as changes in bridge resistance as a result of temperature changes. This feedback system will ensure a linear response to varying pressure.

In a reluctive pressure transducer such as a differential transformer having a movable magnetic core within the transformer, the displacement of the core by the pressure sensing needle provides the desired output signal. The invention is not limited to any one form of pressure transducer, and any type of transducer including the strain gauge type which can be made sufficiently compact to fit within the casing, may be used.

The output signal from transducer 16 is applied to an analog-to-digital converter 23 whose output provides a digital value corresponding to the magnitude of the analog signal and hence to the applied pressure. This digital value is fed to an electronic counter 24 having a hold circuit operated by the hold button switch H and a reset circuit operated by the reset button switch R. Hence, whenever the hold button H is pressed, the digital value in the counter is held at the count attained when the button is pressed. When the reset button R is pressed, counter 24 is reset to zero.

The output of counter 24 is applied to LCD 13 to provide a continuous readout of the values of applied pressure as the pressure applied to the skin of the patient is progressively increased by the examiner. In practice, the display may be calibrated in terms of mg or mm of mercury or water. However, this may not be necessary. Thus, if the display reads from 00 to 99, the range of 1 to 10 can be considered to represent increasing values of slight pressure; 11 to 20, light pressure; 21 to 30, moderate pressure; 31 to 40, heavy pressure; 41 to 50, very heavy pressure; and 51 and above, extreme pressure. Alarm B may therefore be arranged to be activated only when the prevailing pressure exceeds a 50 reading.

In practice, the amplifier for the transducer, the A/D converter, the counter and all other electronic stages preferably take the form of integrated-circuit micro chips. Thus, one may use the type of IC chips forming the movement of a digital electronic stop watch, for these timekeeping circuits include a hold circuit to stop further counting and to hold the existing time indication whenever a stop button is pressed. They also include a reset circuit to return the counter to zero time when a reset button is pressed. These features are the equivalent to those found in mechanical stop watches used for timing races and other events where the elapsed time must be registered. In the present instrument, pressure is converted into a digital value which is held when the sensation of pain is experienced.

Operation of Algesimeter

The electronic algesimeter which is in a pen-like format and incorporates a suitable replaceable battery, is gripped by the examiner during a test procedure between his fingers in the manner of a pen, with the needle more or less at a right angle to the skin at the site to be tested. There is no need to hold the needle in a perfectly vertical position, for the needle encounters no axial friction that will affect the test result if the needle were held at a slant.

In an examination procedure, it is always preferable to first test an unaffected area on the opposite side of the body at the region of interest in order to obtain a normal reference reading of the patient's threshold of pain. After this reference value is obtained, one then tests the affected area to obtain a reading of the threshold value which can then be compared with the reference value to determine the extent of neurological impairment.

The moment the needle engages the skin site and a slight pressure is applied, a reading is obtained, and as the pressure is then slowly increased, the pressure reading becomes progressively greater. The patient is instructed, the moment he feels pain, to say so or to otherwise signal this fact to the examiner and not react by withdrawing the body member being tested.

When the patient signals the examiner that he feels pain, the examiner immediately presses hold button H, thereby retaining the displayed indication. The examiner then withdraws the instrument from the patient and reads the held indication of the threshold value.

In practice, when the examiner makes a note of a given threshold value, he at the same time identifies the skin site of the test and the time and date at which the test was taken so that he then can develop a history of these tests for diagnostic purposes.

Should a given site be insensitive so that the patient then fails to signal the sensation of pain even though the applied pressure is heavy, injury to the patient is avoided by alarm signal B which is activated when the pressure exceeds a safe level. When the alarm is set off, the examiner withdraws the instrument to relieve the pressure.

External Accessories

As shown in FIG. 2, mounted on casing 10 is a female socket 25 adapted to receive a male plug 26 connected by a cable 27 to a hand-held switch 28 external to the instrument. This switch is held by the patient being tested and is pressed by the patient the instant he experiences the sensation of pain.

This plug and socket arrangement acts to bypass the hold button switch $S_1$ on the instrument so that it is remote switch 28 and not the hold button switch H on the instrument that activates the hold circuit. The means for this purpose are similar to those found in transistor radios in which the loudspeaker is cut out of circuit when the terminal plug on the line of an external earphone is plugged into a socket to cause the audio output of the radio to be conducted to the earphone rather than to the loudspeaker.

The advantage of external hold control on the part of the patient is that it does away with any time delay between the patient's signal that he is feeling a pain sensation and the reaction of the examiner to this signal who must then press the hold button. This time delay may result in an erroneous reading of pain threshold value. In this way, the examiner can concentrate on applying pressure to the skin site. The arrangement is such that when the patient presses the hold button 28, this also activates the alarm B to produce a beep which signals the doctor that the patient has just felt pain and the procedure should be stopped.

In order to relieve the examiner from the need to record pain threshold readings obtained with the instrument, a second socket 29 is provided on casing 10 into which one may insert a plug 30 connected by a cable 31 to an external indicator 32, in which case the internal LCD 13 is bypassed.

External indicator 32 provides a pressure indication which is held when hold switch 28 is pressed to provide a threshold pain value which is transferred to a digital alpha-numeric printer 33. This printer, which may be of the type found in many electronic calculators, prints on a paper roll to provide a record of each test and it preferably includes means to print identifying data against each test result.

Associated with the printer is an electronic calendar clock which provides a digital readout of day, date and time. Thus, if the printer is actuated to record a threshold value of, say, 23, the printer will at the same time print the calendar data for this test, say 2:12:85—12:30A, meaning Feb. 12, 1985—12:30 A.M.

The printer may be provided with a keyboard into which the examiner can enter data identifying the patient and the site being tested, so that when the threshold value is being printed, the identifying data is also printed.

In this way, the printout provides a history of the tests conducted on each patient. The external patient hold switch and the external indicator and printer are accessories which are highly useful under normal hospital or office conditions, where they can conveniently be employed. But under emergency conditions, the self-sufficient instrument is all that is necessary, for this makes it possible for a physician to carry out accurate skin sensitivity tests even under the most difficult circumstances without external accessories.

The external hold switch 28, the external display 32 and the digital printer 33, that is, all of the external accessories associated with the primary algesimeter, may be linked thereto by any available cordless remote control system, such as those in use in the remote control of TV sets, telemetric E.C.G. recorders and the like, thereby obviating the need for wired connections and the resultant inconvenience.

While there has been shown and described a preferred embodiment of ELECTRONIC ALGESIMETER in accordance with the invention, it will be appreciated that many changes and modifications may be made therein without, however, departing from the essential spirit thereof. Thus, instead of a digital indicator, the analog voltage from the transducer may be applied to an analog voltmeter in which the needle swings along a scale calibrated in pressure terms, in which case the meter must include a latching button to retain the needle at the threshold value, which button when released, permits the needle to return to the zero point on the scale.

I claim:
1. An algesimeter for determining by cutaneous sensation the pain threshold of a patient being tested, said meter comprising:
   A. a hand-held pressure transducer provided with a sensor constituted by a pointed probe whereby when the point of the probe is pressed against the skin of a patient at a selected site and is shifted from an initial position to a position displaced therefrom that depends on applied pressure, the transducer then yields a signal whose magnitude is a function of the applied pressure, and bias means to maintain said probe at said initial position in the absence of the applied pressure;
   B. means including a resettable electronic pressure indicator responsive to said signal and provided with a display whose reading indicates the magnitude of the signal and hence the degree of applied pressure, said means including an actuatable circuit to hold said reading and a switching device to reset said indicator; and
   C. a manually-operated electrical switch connected to said hold circuit which when actuated renders the circuit effective to hold the reading then being given so that by actuating the switch at the instant the patient who is subjected to the pressure senses pain, the pain threshold value thereof is retained so that it can be read when the probe is withdrawn from the skin, after which the switching device may be operated to reset the indicator.

2. A meter as set forth in claim 1, wherein said indicator is a digital indicator.

3. A meter as set forth in claim 2, in which the transducer yields an analog signal, further including an analog-to-digital converter to convert the analog signal into a corresponding digital value which is applied to said digital indicator.

4. A meter as set forth in claim 3, wherein said transducer is a potentiometric transducer.

5. A meter as set forth in claim 4, wherein said potentiometric transducer forms one arm of a Wheatstone bridge whose output is a direct current signal which varies with the resistance of the transducer.

6. A meter as set forth in claim 5, wherein said bridge includes in another arm a variable resistor to null the bridge.

7. A meter as set forth in claim 3, wherein said transducer is a reluctive device.

8. A meter as set forth in claim 3, wherein said transducer is a strain gauge device.

9. A meter as set forth in claim 1, wherein said transducer and said indicating means are housed in a pen-like casing having a front end and a rear end, and said probe projects axially from the front end of the casing, said casing being provided with a button to reset said indicator and a button to operate said hold switch.

10. A meter as set forth in claim 9, wherein the front end of the casing is covered by a diaphragm from whose outer center the probe projects, the transducer in the casing being coupled to the inner center of the diaphragm.

11. A meter as set forth in claim 9, wherein said indicator includes a liquid crystal display mounted at the rear end of the casing.

12. A meter as set forth in claim 1, further including an alarm indicator coupled to said pressure indicator to provide an alarm signal when the pressure applied to the skin of the patient exceeds a safe level.

13. A meter as set forth in claim 1, wherein said switch is connected to said hold circuit by an extension line whereby the switch may be actuated by the patient being tested when pain is sensed.

14. A meter as set forth in claim 1, wherein said pressure indicator is remote from said transducer, and a digital printer coupled to the output of said remote indicator to print the threshold value when the switch is actuated.

15. A meter as set forth in claim 14, further including a digital calendar clock associated with the printer to provide day, date and time data to the printer so that each time a threshold value is printed, the day, date and time of the test is also printed.

16. A meter as set forth in claim 9, further including a removable cap for said casing to protectively cover the probe.

17. A meter as set forth in claim 1, wherein said probe is a stainless steel needle of standard diameter and length having a point whose wedge is of predetermined slope.

* * * * *